(12) United States Patent
Taylor

(10) Patent No.: US 6,461,596 B1
(45) Date of Patent: Oct. 8, 2002

(54) COMPOSITION AND METHOD FOR PROMOTING HAIR GROWTH

(76) Inventor: Andrea Taylor, 2120 Whippoorwill Rd., Charlottesville, VA (US) 22901-8811

(*) Notice: Subject to any disclaimer, the term of this patent is extended or adjusted under 35 U.S.C. 154(b) by 0 days.

(21) Appl. No.: 08/802,000

(22) Filed: Feb. 18, 1997

(51) Int. Cl.⁷ ............................ A61K 7/06; A61K 31/585
(52) U.S. Cl. ....................................... 424/70.1; 514/175
(58) Field of Search .......................... 424/70.1; 514/175

(56) References Cited

U.S. PATENT DOCUMENTS 3,742,951 A * 7/1973 Zaffaroni ..................... 128/268
4,347,245 A * 8/1982 Shapiro ....................... 514/175

FOREIGN PATENT DOCUMENTS

| EP | 474647 | * | 3/1992 |
| EP | 522157 | * | 1/1993 |
| WO | 9630391 | * | 10/1996 |

* cited by examiner

*Primary Examiner*—Brenda Brumback
(74) *Attorney, Agent, or Firm*—C. Fred Rosenbaum

(57) ABSTRACT

A composition suitable for topical application contains a hair growth promoter integrated into a carrier and a method for local treatment to produce increased hair growth. The composition is composed of an effective amount of spironolactone and an inert oleaginous carrier. The composition may also include ingredients to increase the blood flow about the hair follicles. The composition is applied topically to the area of the body that increased hair growth is desired. The composition is massaged into the skin and remains in place for a minimum of 8 hours. Mild heat may be applied immediately before or after the application to increase blood flow.

2 Claims, No Drawings

COMPOSITION AND METHOD FOR PROMOTING HAIR GROWTH

FIELD OF THE INVENTION

This invention is directed to a composition and a treatment using the composition to increase the visible hair growth in men and women. The term, visible hair, is used to denote the ability of the resultant hair growth to be determined by the naked eye. This distinction is necessary because some people who appear bald to normal sight do have some fine colorless hair. There are two types of hair that concern the adult human. The vellus hair is a short, soft and sometimes pigmented hair that covers the entire body except for the palms of the hands and the soles of the feet. The terminal hair is the coarse, pigmented, longer hair found on the human scalp, face, armpit and pubic regions. It is the relative lack of the latter type that gives the appearance of baldness. The composition and treatment of this invention increase the amount of the terminal hair.

BACKGROUND OF THE INVENTION

In the normal hair growing cycle there are two alternating phases of growth and rest. The growth phases are generally of much longer duration than the rest phases. For example, there may be a growth phase of three to six years and then a rest phase of several months. Then another growth phase starts which replaces the resting hair with a new growing hair. Of course, not all the hair is in the same phase at the same time. Usually, about 10% of the hair on the scalp may be in a resting phase at the same time while the other 90% is in a growth phase. So there is a continual shedding of hair. The problem comes when the shedding out paces the growing hair.

Research has shown that several factors contribute to hair shedding, such as advancing age and inherited tendency to bald early, sometimes referred to as male pattern baldness. Regardless of the names, the shedding of hair without sufficient regrowth afflicts both males and females. With advancing age, there is some evidence that blood circulation about the scalp or hair follicle decreases thereby weakening the follicle and affecting hair growth. In male pattern baldness, the genetically primed follicles diminish in size and produce thinner hairs. The growing phases also become shorter reducing the amount of hair that is grown. With undiminished shedding of hair and the decrease in both size and amount of growth of terminal hair, the condition of baldness soon persists.

Another condition related to hair growth is hirsutism. This over abundance of hair growth is usually more of a concern to women than to men. Facial hair, particularly, is an anathema to most women. This condition has been linked to a hormonal imbalance or genetic predisposition in women who appear to have higher than normal levels of the male hormone, testosterone. Among the many different treatments for this malady is the application of spironolactone to the afflicted area of the body. U.S. Pat. No. 4,347,245 discloses a composition and a treatment for hirsutism. The composition includes spironolactone, a liquid carrier, a solubilizer and a preservative combined as an ointment. The composition is topically applied to the desired area of the body to reduce hirsutism in the selected area.

U.S. Pat. No. 4,684,635 to Orentreich et al discloses a synergistic topical composition of a 5 alpha-reductase enzyme inhibitor and a blocking agent used to treat both hirsutism and male pattern baldness. The blocking agent may be spironolactone.

U.S. Pat. No. 5,061,700 to Dow et al discloses the use of a topical ointment of glyceryl acetate, an oleaginous material, corticosteroid, surfactant, and a thickener for treatment of various conditions. For steroid medicaments delivered to the skin, sex hormones or other steroid compounds, such as spironolactone, may be incorporated in the ointment of the invention. For treatment of disturbances in hair growth, drug substances ,such as minoxidil and antiandrogenic compounds, may be incorporated in the ointment.

U.S. Pat. No. 5,514,672 to Bazzano discloses the use of a retinoid, either orally or topically administered, alone or in combination with other adjunctive compounds to increase the rate of hair growth. Of the different adjunctive compounds used topically, spironolactone is included as one alternative.

None of these patents teach the simple combination of spironolactone with any one of the group of compounds which increase the blood flow about the hair follicles incorporated into a topically applied ointment.

BRIEF SUMMARY OF THE INVENTION

It is an object of this invention to provide a composition in the form of a lotion, salve, ointment, or cream which can be manually applied to the skin of that portion of the body where increased hair growth is desired to produce regrowth of terminal hair. With regard to regrowth of terminal hair, the perception of less baldness and a, "fuller head of hair," can be attributed to the increase of the thickness of the hairs, their length and the number of follicles producing new hair growth. The application of the composition of this invention affects all these attributes.

There are several theories and conditions used to explain hair loss along with resultant medications and processes directed toward these theoretical causes that may regain the lost growth of hair. However, the precise mechanism by which this composition and treatment obtains it's efficacy is not known. What is known is that the continued topical application of an ointment containing spironolactone, and results in increased hair growth. It has also been noted that, in some instances where acne is present, the condition may be alleviated by this treatment.

DETAILED DESCRIPTION OF THE PREFERRED EMBODIMENT

In accordance with the preferred embodiment, the composition of this invention is applied to the desired skin area after the area has been prepared by a thorough cleansing and drying. The composition is then applied to the skin and manually massaged until any excess is absorbed into the skin. The composition should remain undisturbed for at least 8 hours. In some practical tests, the composition remained in place for 24 hours. At the end of this period, the process may be repeated.

To evaluate the results of the use of this composition, several volunteers agreed to use the composition according to the above guidelines. The volunteers ranged in age from 65 to 75 years and had varying degrees of baldness for a number of years. It was determined that in all other respects, their general health did not relate to their loss of hair. After two to four months of continuous treatment, the volunteers exhibited a visually perceptible and measurable increase in hair growth.

The following compositions were evaluated:

| Ingredients | Example 1 | Example 2 | Example 3 | Example 4 | Example 5 | Example 6 |
|---|---|---|---|---|---|---|
| Carrier | 100.0 g | 100.0 g | 100.0 g | 100.0 g | 100.0 g | 100.0 g |
| Spironolactone | 100.0 mg | 200.0 mg | 200.0 mg | 200.0 mg | 200.0 mg | 200.0 mg |
| nitroglycerin | 0.4 mg | | | | | |
| isosorbide mononitrate | | 15.0 mg | | | | |
| terazosin | | | | 2.0 mg | | |
| propranolol | | | | | 20.0 mg | |
| *Capsicum annum* (Capsicin) | | | | | | 25.0 mg |

The carrier selected was a conventional skin care cream available as an off the shelf item. Examples of such a carrier include POND'S, Tm cold cream. The carrier functions as a vehicle for the medicament. The Examples would normally be consumed in about 30 days of treatment. Because of the differing sizes of the areas treated by each individual, the consumption will vary somewhat. As can be established by these parameters, the total daily dose is about 3340 mg to 10,020 mg with the spironolactone being from about 3.3 to 19.8 mg and the other ingredients to being substantially less depending on which specific ingredient is included.

The other ingredients promote blood circulation in the area of the hair follicles. This counteracts the lessening blood flow related to aging and the increased blood flow aids in the uptake of the medicament. With regard to the specific derivative of the Species *Capsicum annum* used, the effective amount is that which results in a mild feeling of warmth in the area to which the omposition is applied.

While various embodiments and modifications of the invention have been described in the foregoing description, further modifications will be apparent to those skilled in the art. Such modifications are included within the scope of this invention as defined by the claims.

I claim:

1. A composition for stimulating hair growth to treat baldness due to aging and genetic predisposition, said composition consisting of an oleaginous carrier, an effective amount of spironolactone, and an effective amount of any one of the group consisting of nitroglycerin, isosorbide, mononitrate, terazocin, propranolol, and capsicin, said composition being applied topically.

2. A method to treat baldness due to aging and genetic predisposition comprising the steps of:

preparing a composition of oleaginous carrier, an effective amount of spironolactone, and an effective amount of any one of the group consisting of nitroglycerin, isosorbide nitrate, terazosin, propranolol and capsicin by intimate admixture;

topically applying about 3340 to 10,020 milligrams of said composition daily in bald area; and repeating said topical application for about thirty consecutive days.

\* \* \* \* \*